United States Patent
Thieking et al.

[11] Patent Number: 6,137,006
[45] Date of Patent: Oct. 24, 2000

[54] PREPARATION OF TRI-IODO BENZENE COMPOUNDS

[75] Inventors: William Thieking, Rensselaer, N.Y.; Einar Odd Ingvoldstad, Spangereid; Trygve Gulbrandsen, Kolsas, both of Norway

[73] Assignee: Nycomed Imaging AS, Oslo, Norway

[21] Appl. No.: 09/436,654

[22] Filed: Nov. 9, 1999

Related U.S. Application Data

[63] Continuation of application No. PCT/GB98/01491, May 22, 1998, which is a continuation-in-part of application No. 60/049,177, Jun. 10, 1997.

[30] Foreign Application Priority Data

May 23, 1997 [GB] United Kingdom .................. 9710728

[51] Int. Cl.$^7$ ........................ C07C 233/00; C07C 22/00
[52] U.S. Cl. ........................ 564/156; 564/163; 570/206
[58] Field of Search ........................ 570/206; 564/163, 564/156

[56] References Cited

FOREIGN PATENT DOCUMENTS

| 2 354 316 | 6/1978 | France . |
| WO 89 09766 | 10/1989 | WIPO . |
| WO 91 01296 | 2/1991 | WIPO . |
| WO 96 37461 | 11/1996 | WIPO . |

OTHER PUBLICATIONS

Haavaldsen J. et al., "X–Ray Contrast Agents. I. Synthesis of Some Deriviatives of 5–Amino–2, 4, 6–Triiodoisophthlamide", ACTA Pharmaceutica Suecica, 20:3, 1983, XP002052827.

Primary Examiner—Alan Siegel
Attorney, Agent, or Firm—Bacon & Thomas

[57] ABSTRACT

The invention provides a process by which ultra low salt content triiodinated aromatic compounds may be isolated from a highly acidic hot triiodination raction medium in a straightforward fashion. The process involves increasing the pH to above 5 with sodium hydroxide, addition of sodium bisulphite and/or sodium dithionite, addition of seed crystals, cooling slowly, and washing the collected precipitate with water.

6 Claims, No Drawings

PREPARATION OF TRI-IODO BENZENE COMPOUNDS

This application is a continuation of pending international application number PCT/GB98/01491 filed May 22, 1998 (of which the entire disclosure of the pending, prior application is hereby incorporated by reference), which itself is a continuation-in-part of U.S. provisional application number 60/049,177 filed Jun. 10, 1997, benefit of which is claimed under 35 U.S.C. 119(e).

This invention relates to a process for the preparation of compounds containing triiodinated benzene rings, eg. iodinated X-ray contrast agents and key intermediates therefor, especially 2,4,6-triiodo-5-amino-benzamides, in particular 2,4,6-triiodo-5-amino-isophthalamides such as 2,4,6-triiodo-5-amino-N,N'-bis(2,3-dihydroxypropyl)-isophthalamide, and to low salt versions of the products produced in the triiodination reactions.

The use in X-ray imaging, eg. CT imaging, of iodinated compounds as contrast agents is well established. Such compounds generally contain one or two triiodinated benzene rings and examples of such compounds include iohexol, iopentol, iodixanol, iopamidol and ioversol. The compounds containing a single iodinated benzene ring are commonly referred to as monomers whereas those containing two iodinated benzene rings are referred to as dimers.

In order that the iodinated contrast agents should be water-soluble, the benzene ring is further substituted by solubilizing groups, eg. carboxyl groups, hydroxylated N or C substituted amide groups, or hydroxyalkyl groups.

Such iodinated agents are generally produced in two stages; in the first stage, primary production, the chemical drug substance is produced in a multistep synthesis; in the second stage, secondary production, the drug substance is formulated to produce the drug product. In primary production, the products of the individual synthetic steps are generally thoroughly purified before subsequent synthetic steps and finally before secondary production. As in any commercial drug preparation, it is important to optimize the yields of the reaction steps, to reduce impurity formation, to reduce wastage of reagents, especially of expensive reagents, and to optimize the efficiency of energy and equipment usage.

In the production of iodinated X-ray contrast agents, the iodinating agents (usually iodine halides such as $NaICl_2$ or $KICl_2$) are expensive and iodination of the aromatic ring is usually performed in a relatively late stage of the multistep synthesis so as to reduce wastage of the iodinating agent.

Thus in the preparation of many commercial X-ray contrast agents (eg. iopamidol, ioversol, iomeprol, iopentol, iodixanol and iohexol), a key reaction step is the 2,4,6-triiodination of a 2,4,6-unsubstituted benzene ring containing compound, eg. a 5-amino-benzamide (an "AB"). In the case of iohexol, iopentol and iodixanol the 5-amino benzamide is 5-amino-N,N'-bis(2,3-dihydroxy propyl) isophthalamide which is iodinated to produce, 5-amino-2,4,6-triiodo-N,N'-bis(2,3-dihydroxypropyl)-isophthalamide (compound A).

The iodination of the AB is carried out in an aqueous reaction medium at a moderately low pH using an iodine halide and generates mineral acid by-products. Thus at the end of the iodination reaction the reaction mixture contains large amounts of mineral acid. Since the triiodo-ABs commonly contain acid/alkali sensitive side chains and are acid soluble aniline derivatives, the reaction medium is normally neutralised with a base such as sodium hydroxide prior to isolation of the triiodo-AB product. Salts formed in the neutralization precipitate with the organic product and can account for several percent of the product weight.

Examples of the triiodination reaction using iodine halides may be found in SE7706792-4, US-A-3145197, WO89/09766, WO91/01286 and the article by Haavaldsen et al. in Acta Pharc. Suec. 20: 219–232 (1983).

Preparation of a substantially salt free product requires further handling, eg. recrystallisation from water or a suitable hydroxylated solvent (eg. a lower alkanol). This adds to the number of handling steps in the overall synthesis, generates further waste products, reduces overall yield, adds further equipment requirements, extends overall process duration and thus adds to the expense of drug substance production.

Using such recrystallisation techniques, the purified triiodo-AB generally still has a residual salt content (usually sodium chloride) of 0.1 to 1% w/w.

We have now found that the triiodo-AB can be precipitated in a substantially salt free form by a novel precipitation procedure, thereby reducing the amount of work up required and improving performance of subsequent reaction steps.

Thus viewed from one aspect the invention provides a process for the preparation of a 2,4,6-triiodinated benzene ring containing compound which comprises iodinating a 2,4,6-unsubstituted benzene ring containing compound with an iodine halide iodinating agent in a aqueous reaction medium at a pH below 4 and precipitating the triiodinated reaction product, characterised in that precipitation of the triiodinated reaction product is effected by: adding an aqueous base (eg. sodium hydroxide) to the reaction medium while this is at a temperature in the range 70 to 95° C., thereby to bring the pH of the reaction medium to above 5; adding a reducing agent (e.g. sodium bisulphite or sodium dithionite) to the reaction medium while agitating the reaction medium; adding seed crystals of the triiodinated reaction product to the reaction medium; cooling the reaction medium to a temperature below 35° C., eg. in the range 15 to 35° C., preferably about 30° C., over a period of 10 to 30 hours, at a cooling rate of 1.5 to 5° C./hour during the period during which precipitation occurs; filtering the reaction medium to collect the precipitated triiodinated reaction product; and washing the precipitated triiodinated reaction product with from 70 to 200% by weight relative to the weight of the precipitated triiodinated reaction product of water, whereby to yield a product having a salt (eg. sodium halide) content of less than 0.1% by weight, preferably less than 0.05%.

The 2,4,6-unsubstituted starting reagent for the triiodination is preferably a 5-amino-benzamide, particularly one which is alkylated at the amide nitrogen, preferably by a $C_{1-6}$ straight chain or branched alkyl group, particularly a hydroxylated alkyl group, eg. a group containing up to 6 hydroxyl groups especially a group containing 2, 3 or 4 hydroxyl groups, eg. a 2,3-dihydroxypropyl, 1,3,4-trihydroxy-but-2-yl, 1,3-dihydroxyprop-2-yl, 1,3-dihydroxy-2-hydroxymethyl-prop-2-yl, 2,3,4-trihydroxy-butyl, or 2-hydroxy-ethyl group. Particularly preferably the 5-amino-benzamide is a 5-amino-isophthalamide and especially preferably both amide nitrogens are substituted as discussed above for the benzamide amide nitrogen. Alternatively the 5-amino-benzamide may be a 5-amino-N-alkyl-isophthalamic acid or a salt or ester thereof, preferably a compound in which the N-alkyl group is as discussed above for the 5-amino-benzamides.

Especially preferably the 5-amino-benzamide is 5-amino-N,N'-bis(2,3-dihydroxypropyl)-isophthalamide, a key intermediate in the production of iohexol as described in SE 7706792-4 (Nyegaard).

The 5-amino-benzamide is preferably in an initial concentration of 20 to 30% w/w, especially 21 to 27% w/w.

The iodine halide iodinating agent used in the triiodination process is iodine chloride or another iodine halide. This may be produced by adding molecular iodine and another molecular halogen to an alkali metal halide solution, eg. adding $I_2$ and $Cl_2$ to a NaCl or KCl solution. Preparation of $KICl_2$ and $NaICl_2$ in this way is a well established procedure. In the discussion below, iodine chloride will generally be referred to since this, or more particularly $NaICl_2$, is the preferred iodine halide. Nonetheless other iodine halides may be used and the discussion is equally applicable to such other iodine halides.

In the triiodination process, the iodine chloride is preferably added in portions to an aqueous reaction medium which contains the 2,4,6-unsubstituted starting reagent and which is at or is brought to a temperature in the range 40 to 95° C., preferably 50–90° C. The portions of iodine chloride are preferably 30 to 60% w/w, especially preferably 45–52% w/w, particularly about 50% w/w aqueous solutions, the percentages referring to ICl content. The portions may have different concentrations but conveniently all will have substantially the same ICl concentration, preferably about 50% w/w.

The portions should be sufficient to raise the total amount of iodine chloride added to 3.05 to 3.20 equivalents. By one equivalent is meant a molar ratio of 1:3 of iodine chloride to iodination sites of which there are three (positions 2, 4 and 6) on the 5-amino-benzamide.

The portions will generally each be added over a period of 3 to 10 minutes depending on the quantity being added.

For the addition of the initial portion, the pH of the reaction mixture to which it is added is preferably adjusted to 2.0 to 3.5, especially preferably about 3.0, eg by addition of sodium hydroxide. For subsequent portions the pH is preferably adjusted by addition of base to 1.5 to 2.5, preferably about 2. During the reaction the pH will vary, eg. from 3 to 0 or even −1 from the beginning to the end point after each portion addition.

After the final portion of iodine chloride is added the reaction is allowed to proceed until the remaining iodine chloride content of the reaction medium is in the range 0.20 to 0.90% w/w. Overall reaction time will generally be in the range 6 to 20 hours, preferably about 8 to 14 hours.

The reaction is then quenched and the triiodinated product precipitated using the process of the invention. The precipitated 2,4,6-triiodinated product is then optionally dried and stored or is used further, eg. in N-alkylation and N-acylation reactions to introduce optionally hydroxylated $C_{1-6}$-alkyl and optionally hydroxylated $C_{1-6}$-alkyl-carbonyl groups at the 5-amino nitrogen or a coupling reaction to produce a dimeric product. Processes which take the 2,4,6-triiodinated product of iodination and react these further, eg. to produce a chemical drug substance, are deemed to fall within the scope of the process of this invention.

Work-up and further reaction such as described above may be effected in a conventional manner well known to those skilled in the art.

During the iodination reaction, the pH, temperature iodine halide content and the contents of the mono-, di- and tri-iodinated products of the reaction mixture should preferably be monitored, either continuously or on a repeated sampling basis, eg. using known spectroscopic or chromatographic techniques. pH or temperature variations may be compensated for by acid or base addition and by heating or cooling. Iodine halide variation will, as discussed above, determine the timing of iodine halide portion addition and termination of the reaction.

In the precipitation process, the aqueous base (eg. sodium hydroxide) is preferably at a concentration of 15 to 50% and a temperature substantially similar to that of the reaction medium which is preferably 75 to 85° C., especially preferably 80° C. Sufficient base is added to bring the pH to a value in the range 3 to 7, especially 3 to 5. The base may be added in one or several portions, eg. over a period of 15 minutes to 2 hours.

The reducing agent (eg. sodium bisulphite and/or sodium dithionite) is preferably added in aqueous solution in quantities of 0.10 to 0.50 moles per mole of triiodinated product, again either in one or several portions, preferably over a period of 15 to 50 minutes. The solutions added will preferably be at the same temperature as the reaction medium.

During the addition of the reducing agent, the reaction medium is agitated, eg. stirred using rotating paddles or a magnetic stirrer bar.

Following addition of the reducing agent, and before precipitation of the triiodinated product begins, seed crystals, eg. 0.001 to 0.05 g/g of the initial 2,4,6-unsubstituted reactant, are added to promote precipitation. The seed crystals are crystals of the 2,4,6-triiodinated product, eg. in the first instance produced by conventional precipitation, washing and recrystallisation processes but subsequently preferably crystals produced by the process of the invention. In the case of 5-amino-2,4,6-triiodo-N,N'-bis (2,3-dihydroxypropyl)isophthalamide these are preferably crystals of the yellow polymorph which is formed when it is precipitated from aqueous solution by cooling at a rate less than 7° C./hour.

The reaction mixture is then cooled relatively slowly from a temperature in the range 70 to 95° C., preferably 75 to 85° C., especially preferably about 80° C., to a temperature below 35° C., preferably to about 30° C. The cooling takes place over a period of 10 to 30 hours, preferably 15 to 25 hours at a rate of 1.5 to 5° C./hour at least during the period in which precipitation occurs, but preferably throughout this cooling period. At this stage the reaction mixture will generally be transferred to filtration apparatus. The reaction mass is filtered and the cake of triiodinated reaction product is smoothed and mended (ie. to remove cracks).

The cake is then washed with water, preferably water having a salt content of less than 1 ppm, eg. deionized water, with the cake again being smoothed and mended during the washing step. Washing is preferably carried out 3 to 7 times, especially 4 to 6 times, using fresh portions of water. The water portion size is preferably 15 to 40%, more preferably 20 to 35%, of the mass of the reaction product (eg. the dry weight of the precipitated product). The water is preferably at a temperature of 10 to 30° C., especially about 20° C. The product can then be dried, eg. at 60° C., before being stored or used in further reaction steps as discussed above. Typically the salt content (eg. NaCl content) of the triiodinated product thus prepared is in the range 100 to 300 ppm (ie. 0.01 to 0.03% w/w).

Given the high initial salt content of the reaction medium following addition of the aqueous base (eg. sodium hydroxide) it is very surprising that such low salt contents can be achieved with such little washing and without requiring recrystallisation.

This low salt content means that subsequent reaction products can be produced with lower than conventional levels of impurities.

Such low salt content triiodo-AB products have not previously been produced and form a further aspect of the invention. Viewed from this aspect the invention provides a 5-amino-2,4,6-triiodo-benzamide, especially a 5-amino-2,4,6-triiodo-N-alkyl-isophthalamide, more especially 5-amino-2,4,6-triiodo-N,N'-bis(2,3-dihydroxy-propyl)isophthalamide, having an alkali metal halide salt content of less than 0.05% w/w, especially 0.005 to 0.04% w/w, particularly 0.01 to 0.03% w/w.

The invention will now be described further with reference to the following Examples:

EXAMPLE 1

A crude solution of 5-amino-2,4,6-triiodo-N,N'-bis(2,3-dihydroxypropyl)-isophthalamide (A) was prepared from 90 g 5-amino-N,N'-bis(2,3-dihydroxypropyl)isophthalamide HCl salt (prepared according to the method of Haavaldsen et al. in Acta. Pharm. Suec. 20: 219–232 (1983)). Iodine chloride, 3.15 equivalents to the isophthalamide, was added in 4 steps to the reaction mixture and kept at 60–85° C. pH was kep between 3–0.5 throughout the synthetic part of the reaction. To terminate the reaction 2.3–4.5 g of sodium metabisulphite was added at 70–80° C. to the crude solution of (A) and the mixture was basified to pH 3–5 with 50% caustic solution. Thereafter 1.0–2.5 g sodium dithionite was added and the batch was treated with 0.9 g seed at 78–82° C. and held at 80° C. for 2–3 hours to crystallize. The batch was cooled at 5° C. per hour until 15–30° C. and then further chilled and filtered.

The filtercake was washed with up to 50 ml water and then combined with a 10 ml rinse, filtered and washed 4 times with 50 ml water and two times with isopropanol The products was vacuum dried to yield 169 g product (A). The salt concentration in the final product was 0.015% w/w.

What is claimed is:

1. A process for the preparation of a 2,4,6-triiodinated benzene ring containing compound which comprises iodinating a 2,4,6-unsubstituted benzene ring containing compound with an iodine halide iodinating agent in an aqueous reaction medium at a pH below 4 and precipitating the triiodinated reaction product, characterised in that precipitation of the triiodinated reaction product is effected by: adding an aqueous base to the reaction medium while this is at a temperature in the range 70 to 95° C., thereby to bring the pH of the reaction medium to above 5; adding a reducing agent to the reaction medium while agitating the reaction medium; adding seed crystals of the triiodinated reaction product to the reaction medium; cooling the reaction medium to a temperature below 35° C. over a period of 10 to 30 hours, at a cooling rate of 1.5 to 5° C./hour during the period during which precipitation occurs; filtering the reaction medium to collect the precipitated triiodinated reaction product; and washing the precipitated triiodinated reaction product with from 70 to 200% by weight relative to the weight of the precipitated triiodinated reaction product of water, whereby to yield a product having a salt content of less than 0.1% by weight.

2. A process as claimed in claim 1 wherein said 2,4,6-unsubstituted compound is a 5-amino-benzamide.

3. A process as claimed in claim 2 wherein said 5-amino-benzamide is a 5-amino-N,N'-bisalkyl-isophthalamide.

4. A process as claimed in claim 1 wherein said 5-amino-benzamide is a 5-amino-N,N'-bis(2,3-dihydroxypropyl)-isophthalamide.

5. A process as claimed in claim 1 wherein said iodine halide is iodine chloride.

6. The process of claim 1 wherein said product has a salt content of less than 0.05%.

* * * * *